United States Patent
Liu et al.

(10) Patent No.: US 9,855,250 B1
(45) Date of Patent: Jan. 2, 2018

(54) METHOD TO TREAT LUNG CANCER

(71) Applicant: Macau University of Science and Technology, Macau (CN)

(72) Inventors: Liang Liu, Macau (CN); Elaine Lai-Han Leung, Macau (CN); Xiao-Jun Yao, Macau (CN); Vincent Kam-Wai Wong, Macau (CN); Xi Chen, Macau (CN)

(73) Assignee: Macau University of Science and Technology, Macau (CN)

( * ) Notice: Subject to any disclaimer, the term of this patent is extended or adjusted under 35 U.S.C. 154(b) by 0 days.

(21) Appl. No.: 15/351,419

(22) Filed: Nov. 14, 2016

(51) Int. Cl.
*A61K 31/4245* (2006.01)

(52) U.S. Cl.
CPC .................. *A61K 31/4245* (2013.01)

(58) Field of Classification Search
CPC .................................................. A61K 31/4245
USPC ......................................................... 514/364
See application file for complete search history.

(56) References Cited

PUBLICATIONS

Wang et al. Oncology Letters, (2014), 8(3), p. 1039-1042.*
CAS RN 1190003-70-3 on Oct. 25, 2009 by Aurora Fine Chemicals.*
Fryer, L. G., Parbu-Patel, A., & Carling, D. (2002). The anti-diabetic drugs rosiglitazone and metformin stimulate AMP-activated protein kinase through distinct signaling pathways. Journal of Biological Chemistry, 277(28), 25226-25232.
Hotamisligil, G. S. (2006). Inflammation and metabolic disorders. Nature, 444(7121), 860-867.
Ji, H., et al. (2007). LKB1 modulates lung cancer differentiation and metastasis. Nature, 448(7155), 807-810.
Santos, C. R., & Schulze, A. (2012). Lipid metabolism in cancer. Febs Journal, 279(15), 2610-2623.
Praveen, P., et al. (2016). Cross-talk between AMPK and EGFR dependent Signaling in Non-Small Cell Lung Cancer. Scientific Reports, 6, 27514.
Rehman, G., et al. (2014). Role of AMP-activated protein kinase in cancer therapy. Archiv der Pharmazie, 347(7), 457-468.
American Cancer Society. (2015). Cancer Facts & Figures 2015.
Jin, Q., et al. (2007). Implication of AMP-activated protein kinase and Akt-regulated survivin in lung cancer chemopreventive activities of deguelin. Cancer research, 67(24), 11630-11639.
Wang, Y., et al. (2012). Cardiac glycosides induce autophagy in human non-small cell lung cancer cells through regulation of dual signaling pathways. The international journal of biochemistry & cell biology, 44(11), 1813-1824.
Siejka, A., Barabutis, N., & Schally, A. V. (2011). GHRH antagonist MZ-5-156 increases the expression of AMPK in A549 lung cancer cells. Cell Cycle, 10(21), 3714-3718.
Shin, D. H., Choi, Y. J., & Park, J. W. (2014). SIRT1 and AMPK mediate hypoxia-induced resistance of non-small cell lung cancers to cisplatin and doxorubicin. Cancer research, 74(1), 298-308.
Hardie, D. G., & Carling, D. (1997). The AMP-activated protein kinase. European Journal of Biochemistry, 246(2), 259-273.
Hawley, S. A., et al. (2005). Calmodulin-dependent protein kinase kinase-β is an alternative upstream kinase for AMP-activated protein kinase. Cell metabolism, 2(1), 9-19.
Lamberts, R. R., et al. (2009). Reactive Oxygen Species-Induced Stimulation of 5' AMP-Activated Protein Kinase Mediates Sevoflurane-Induced Cardioprotection. Circulation, 120(11 suppl 1), S10-S15.
Russell, R. R., et al. (2004). AMP-activated protein kinase mediates ischemic glucose uptake and prevents postischemic cardiac dysfunction, apoptosis, and injury. The Journal of clinical investigation, 114(4), 495-503.
Birnbaum, M. J. (2005). Activating AMP-activated protein kinase without AMP. Molecular cell, 19(3), 289-290.
Breen D. M., et al (2008). Stimulation of muscle cell glucose uptake by resveratrol through sirtuins and AMPK. Biochemical and biophysical research communications, 374(1), 117-122.
Zhang F. J. et al. (2015). Curcumin inhibits Ec109 cell growth via an AMPK-mediated metabolic switch. Life sciences, 134, 49-55.
Shaw, R. J., et al. (2005). The kinase LKB1 mediates glucose homeostasis in liver and therapeutic effects of metformin. Science, 310(5754), 1642-1646.
Guigas, B., et al. (2007). AMP-activated protein kinase-independent inhibition of hepatic mitochondrial oxidative phosphorylation by AICA riboside. Biochemical Journal, 404(3), 499-507.
Göransson, O., et al. (2007). Mechanism of action of A-769662, a valuable tool for activation of AMP-activated protein kinase. Journal of Biological Chemistry, 282(45), 32549-32560.
Hawley, S. A., et al. (2012). The ancient drug salicylate directly activates AMP-activated protein kinase. Science, 336 (6083), 918-922.
Cool, B., et al. (2006). Identification and characterization of a small molecule AMPK activator that treats key components of type 2 diabetes and the metabolic syndrome. Cell metabolism, 3(6), 403-416.
Huang, X., et al. (2008). Important role of the LKB1-AMPK pathway in suppressing tumorigenesis in PTEN-deficient mice. Biochemical Journal, 412(2), 211-221.
Pang, T., et al. (2008). Small molecule antagonizes autoinhibition and activates AMP-activated protein kinase in cells. Journal of Biological Chemistry, 283(23), 16051-16060.
Watson, J. D. (2014). Type 2 diabetes as a redox disease. The Lancet, 383(9919), 841-843.

(Continued)

*Primary Examiner* — Yong Chu
(74) *Attorney, Agent, or Firm* — Eagle IP Limited; Jacqueline C. Lui (57) ABSTRACT

One example embodiment relates to a method of treating lung cancer by administering a compound of formula I to a subject in need thereof. Another embodiment relates to a method to treat Non-Small Cell Lung Cancer (NSCLC) by administering the compound of formula I to a patient.

formula I

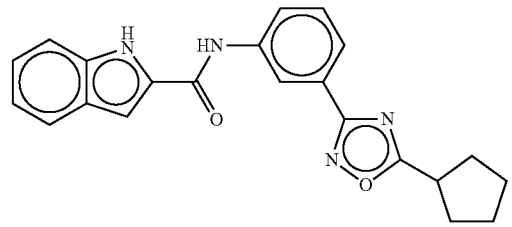

14 Claims, 7 Drawing Sheets
(5 of 7 Drawing Sheet(s) Filed in Color)

(56) References Cited

PUBLICATIONS

Liang, J., & Mills, G. B. (2013). AMPK: a contextual oncogene or tumor suppressor?. Cancer research, 73(10), 2929-2935.

Zhan Y. et al. (2008). Control of cell growth and survival by enzymes of the fatty acid synthesis pathway in HCT-116 colon cancer cells. Clinical Cancer Research, 14(18), 5735-5742.

Hardie D. G., & Pan, D. A. (2002). Regulation of fatty acid synthesis and oxidation by the AMP-activated protein kinase. Biochemical Society Transactions, 30(6), 1064-1070.

Kaminski, G. A., et al. (2001). Evaluation and reparametrization of the OPLS-AA force field for proteins via comparison with accurate quantum chemical calculations on peptides. The Journal of Physical Chemistry B, 105(28), 6474-6487.

Xiao, B., et al. (2013). Structural basis of AMPK regulation by small molecule activators. Nature communications, 4.

A. Woods, D. Vertommen, D. Neumann, R. Turk, J. Bayliss, U. Schlattner, T. Wallimann, D. Carling, M.H. Rider, Identification of phosphorylation sites in AMP-activated protein kinase (AMPK) for upstream AMPK kinases and study of their roles by site-directed mutagenesis, J Biol Chem 278(31) (2003) 28434-42.

D. Moreno, E. Knecht, B. Viollet, P. Sanz, A769662, a novel activator of AMP-activated protein kinase, inhibits non-proteolytic components of the 26S proteasome by an AMPK-independent mechanism, FEBS letters 582(17) (2008) 2650-4.

S.A. Hawley, M. Davison, A. Woods, S.P. Davies, R.K. Beri, D. Carling, D.G. Hardie, Characterization of the AMP-activated protein kinase kinase from rat liver and identification of threonine 172 as the major site at which it phosphorylates AMP-activated protein kinase, J Biol Chem 271(44) (1996) 27879-87.

* cited by examiner

METHOD TO TREAT LUNG CANCER

FIELD OF THE INVENTION

The present invention relates to a method of treating lung cancer. In particular, the present invention relates to a method of treating Non-Small Cell Lung Cancer (NSCLC).

BACKGROUND

Lung cancer is one of the most lethal cancers worldwide. Non-Small Cell Lung Cancer (NSCLC) is any type of epithelial lung cancer other than small cell lung carcinoma (SCLC). NSCLC accounts for about 85% of all lung cancers.

In view of the demand for effectively treating lung cancers including NSCLC, improvements in method and compositions that treat lung cancers or NSCLC are desired.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

One example embodiment is a method of treating lung cancer in a subject in need thereof. The method includes administering to the subject a therapeutically effective amount of a compound of formula I to treat the lung cancer. Another example embodiment is a method of treating Non-Small Cell Lung Cancer (NSCLC) that includes administering to a subject in need thereof a compound of formula I.

Other example embodiments are discussed herein.

DETAILED DESCRIPTION

Example embodiments relate to methods and compounds to treat lung cancer by administering the compound with the following formula I to a patient. Example embodiments also relate to methods to treat Non-Small Cell Lung Cancer (NSCLC) by administering the compound of formula I to a patient.

formula I

In one embodiment for example, the compound of formula I activates 5'-adenosine monophosphate-activated protein kinase (AMPK) and in turn treats lung cancer or NSCLC.

AMPK is a trimeric enzyme consisting of three subunits, i.e., one catalytic subunit α and two regulatory subunits β and γ. AMPK acting as a major cellular energy sensor, regulates metabolic homeostasis. Upon activation, AMPK induces a series of intracellular metabolic changes to balance energy consumption and production. The activation of AMPK results in multiple downstream signaling pathways to control nutrient uptake and energy metabolism.

AMPK plays an important role in tumor pathogenesis and is also considered as a target of NSCLC. Some target therapies for NSCLC shows fantastic effect initially, for example, targeting on epidermal growth factor receptor (EGFR); however, unfortunately the resistance has appeared because EGFR develops additional mutation.

The activation of AMPK regulates its downstream channels through the cascade (e.g. Acetyl-CoA carboxylase (ACC), mechanistic target of rapamycin (mTOR), Tuberous sclerosis 1/2 (TSC1/2)) to induce NSCLC cell death by regulating material and energy situation. AMPK affects cell cycle, cell proliferation, and cell survival, and is also involved in the regulation of mitochondrial biogenesis on NSCLC. AMPK responds to an increased adenosine monophosphate (AMP)/adenosine triphosphate (ATP) ratio by turning on ATP-generating pathways, while turning off ATP-consuming ones. It directly switches from an anabolic to a catabolic state to save emergency of lack energy. Thus, AMPK could be activated by its upstream Ser/Thr protein kinase, mainly the tumor suppressor liver kinase beta 1 (LKβ1) and the calcium/calmodulin-dependent protein kinase kinase-β (CaMKKβ), low energy status (e.g. lack of oxygen, glucose and ATP), and other AMPK activators. The mechanism of activating AMPK is ultimately to phosphate Thr 172 site within α-subunit.

There are lots of AMPK activators, which are divided into 2 types, direct and indirect AMPK activators, according to their different effective sites on AMPK structure. The indirect activators (e.g 2-Deoxy-D-glucose (2DG), resveratrols, biguanides, curcum in, 5-Aminoimidazole-4-carboxamide ribonucleotide (AICAR)) activate AMPK via activation its upstream to achieve and some of them are used in clinical. However, these activators are known to have additional molecular targets and AMPK-independent effects. The direct activators (e.g. A-769662, Salicylate) cause allosteric activation of AMPK via directly effecting AMPK's subunits. For example, A-769662 (Abbott Laboratories) has initially shown promising results in the treatment of metabolic disorders and cancer. However, it has been recently reported that A-769662 shows the cytotoxicity by AMPK-independent mechanism as side effects.

Example embodiments provide a compound of formula I as an original direct AMPK activator that is used to treat lung cancer or NSCLC. The compound exhibits significant inhibitory effect on Gefitinib-resistant cell lines H1975 with $EGFR^{L858R/T790M}$ double mutations, but not normal lung fibroblast cells CCD-19 Lu. The compound significantly activates AMPK enzyme in vitro assay. The compound directly enhances the expression of phosphate-AMPK. The compound inhibits ACC to suppress fatty acid syntheses, leading to cell cycle arrest and in turn induce apoptosis of cancer cells.

Example 1

Material and Methods

1. Materials

The compound F321-0719 with formula I was purchased from Top Science Co. Ltd (Shanghai, China). (3-(4,5-Dimethylthiazol-2-yl)-2,5-diphenyltetrazolium bromide (MTT) powder and Dimethyl sulfoxide (DMSO) were purchased from Acros Organics (Morris Plains, N.J., USA). Adenosine 5'-Triphosphatase was purchased from Sigma Aldrich (St. Louis, Mich., USA). Radioimmunoprecipitation (RIPA) lysis buffer (10×) and the primary antibodies of p-ACC, ACC were purchased from Cell Signaling Technology (Danvers, Mass., USA). The primary antibodies of p-AMPK, AMPK and β-actin were purchased from Santa Cruz (Dallas, Tex., USA). The secondary antibodies of anti-rabbit and anti-mouse were purchased from Odyssey (Belfast, Me., USA). Fluorescein-conjugated goat anti-rabbit and mouse antibodies were purchased from Odyssey (Belfast, Me., USA) and Invitrogen (Waltham, Mass., USA). Propidium iodide (PI) staining kit was purchased from BD Biosciences (San Jose, Calif., USA). RNase A was purchased from Sigma Aldrich (St. Louis, Mich., USA). Ten percent fetal bovine serum (FBS), 100 U/ml penicillin and 100 µg/ml streptomycin which were purchased from Gibco (Oklahoma, ME, USA). A complete mini, EDTA-free tablet was purchased from Roche (Mennheim, Germany). DCTM protein assay kit was purchased from Bio-Rad (Hercules, Calif., USA). Nitrocellulose (NC) membrane was purchased from GE Healthcare (Waukesha, Wis., USA).

2. Methods 2.1 Molecular Docking Study on the Interaction Between the Compound F321-0719 and AMPK The 3D structure of the compound F321-0719 was obtained from the Chemdiv database. Then, the 3D structure was preprocessed by the LigPrep which uses OPLS-2005 force field and gave the corresponding low energy 3D conformers of the compound. The ionized state was assigned by using Epik at a target pH value of 7.0±2.0. The 3D crystal structure of the adenosine 5'-monophosphate (AMP)-activated protein kinase (AMPK) for molecular docking was retrieved from the Protein Data Bank (PDB ID 4CFE). The Protein Preparation Wizard was used to remove crystallographic water molecules, add hydrogen atoms, assign partial charges using the OPLS-2005 force field, assign protonation states, and minimize the structure. The minimization terminated when the root-mean-square deviation (RMSD) reached a maximum value of 0.3 Å. The compound F321-0719 was docked into the binding site of the AMPK using the Glide with the standard precision (SP) scoring mode. The docking grid box was defined by centering on the compound 991 in the complex. In the molecular docking, 500 poses were generated during the initial phase of the docking calculation, out of which best 100 poses were chosen for energy minimization by 1000 steps of conjugate gradient minimizations.

2.2 Cell Culture

H1975 and CCD-19 Lu was purchased from ATCC (American type culture collection). H1975 was cultivated with RPMI 1640 medium supplement with 10% fetal bovine serum (Gibco, Big Cabin, Okla., ME, USA), 100 U/mL, penicillin and 100 µg/mL and streptomycin (Gibco, Big Cabin, Okla., ME, USA). CCD-19 Lu was cultivated with MEM medium supplemented with 10% FBS, 100 U/ml penicillin and 100 µg/ml streptomycin. All cells were cultivated at 37° C. in a humidified atmosphere of 5% $CO_2$.

2.3 MTT Cytotoxicity Assay

H1975 cells were seeded in a 96-well microplate with 3000 cells/well confluence, and put into the incubator overnight for cells adhesion. Different concentrations of the compound F321-0719 were added with Dimethyl sulfoxide (DMSO) as vehicle control. The microplates were incubated for further 72 h. Each dosage was repeated in triplicate. 10 µL of MTT (5 mg/mL) solution was added to each well. The plate was placed back into the incubator for 4 hours. After that, 100 µL of resolved solution (10% SDS and 0.1 mM HCL) was added to each well. Before dissolving the formazan crystals, the microplate was put back into the incubator for another 4 hours. The absorbance of the plate was measured at 570 nm with reference 650 nm by a microplate reader (Tecan, Morrisville, N.C., USA). Cell viability was calculated by percentages of the absorbance of the treatment group divided by the absorbance of untreated group. At least three independent experiments were performed for data analysis and presentation.

2.4 Apoptosis Assay

H1975 cells (1×10$^5$ cells/well) were seeded in a 6-well plate for 24 h, and treated with the indicated concentrations of the compound F321-0719 for an additional 48 h at 37° C. After 48 h, the cells were washed by ice-cold 1×PBS (Phosphate-buffered saline) once and harvested by trypsination. Then cells were centrifuged, collected and re-suspended in ice-cold 1×PBS. After removing the supernatants, cell pellets were re-suspended in 100 µL 1× Annexin-binding buffer. The cells were then double-stained with Annexin-V FITC and PI (100 µg/mL) of 2 µL respectively for 15 min at room temperature in dark. After that, 300 µL 1× Annexin-binding buffer was added. Apoptotic cells were quantitatively counted by a BD Aria III Flow Cytometer (BD Biosciences, San Jose, Calif., USA).

2.5 Cell Cycle Analysis

H1975 cells were plated with 1.5×10$^5$ cells/well at a 6-well plate and cultured overnight for attachment. Cells were treated with the compound F321-0775 at 0, 2.5, 5, 10 µM for 48 h. After treatment, all cells were harvested by trypsinization, and collected by centrifugation. After removing all suspension, cells were washed by PBS. Cells pellets were re-suspended in 70% ethanol at 4° C. overnight. Cells were centrifuged at 1000 rpm for 5 min to remove all the ethanol. Each cell pellet was re-suspended in 500 µl PI staining solution at 37° C. for 30 min in dark. Then, they were washed in PBS twice. Cells were re-suspended in 300 µl 1× binding buffer and transferred to the flow cytometer (BD FACS Aria III).

2.6 Western Blot Analysis

After incubating H1975 cells with the compound F321-0719 for 24 h, H1975 cells were harvested and washed with cold 1×PBS. Then, cells were lysed with ice-cold RIPA lysis buffer with protease and phosphatase inhibitors added to extract the cell protein extraction. The supernatants were collected by centrifugation at 12,000 g, for 5 minutes. The quantitation of total protein extraction was measured by Bio-Rad DCTM protein assay kit (Bio-Rad, Philadelphia, Pa., USA). Then 30 µg of protein were loaded and electrophoretically separated on 10% SDS-PAGE gel and then transferred to Nitrocellulose (NC) membrane. Membranes were blocked with 5% non-fat milk and PBS containing 0.1% Tween-20 (TBST) for 1 hour at room temperature. After 1 hour, membranes were incubated with primary antibodies (1:1000 dilution) against β-actin, total/phosphor-ACC, total-AMPK, and against phosphor-AMPK, at 4° C. with gently shaking overnight. Membranes were washed with TBST for 3 times (5 minutes/time), and incubated with secondary fluorescent antibody (1:10000 dilutions) for 1 hour at room temperature. Rewashing with TBST for 3 times (15 minutes/time), the stripes were visualized by LI-COR Odessy scanner (Belfast, Me., USA).

2.7 AMPK Enzyme Activity Assay

The CycLex AMPK Kinase Assay Kit (CycLex Co., Ltd., Nagano, Japan) was used to detect the activation of AMPK by the compound F321-0719. Compound C was used as AMPK inhibitor, and AMPK active enzyme was used as a positive control for phosphorylation.

2.8 Statistical Analysis

All data represent mean values of at least three independent experiments and were expressed as mean±SEM. The statistical significant differences were analyzed by one-way ANOVA for comparison tests, using Graph Prism Version 6.0 software (San Diego, Calif., USA). $*p<0.05$, $p<0.01$, $*p<0.001$ were considered as significant.

Figure 1:
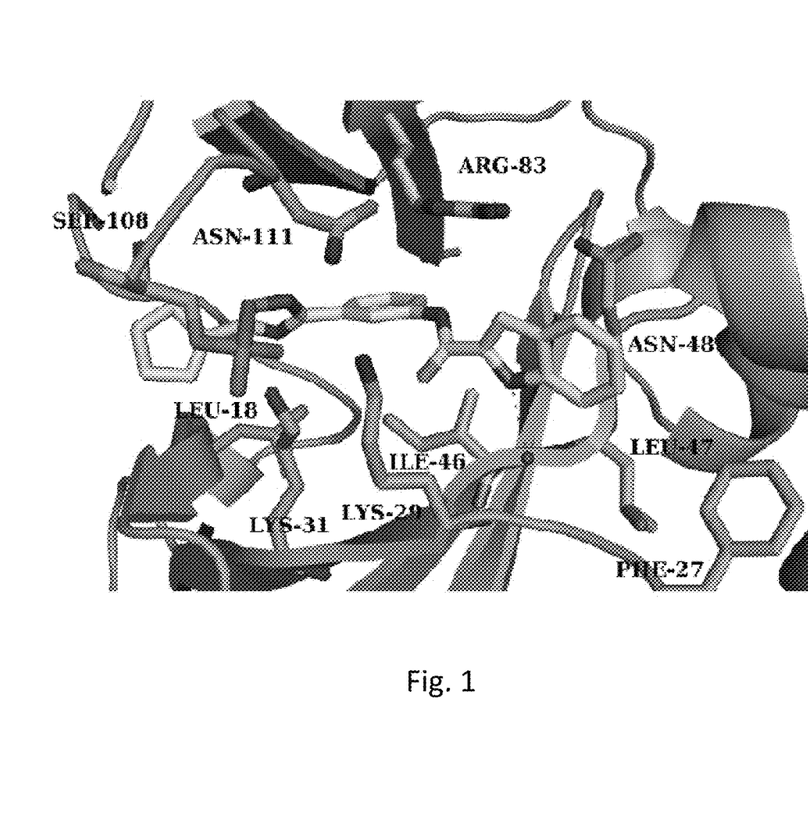
FIG. 1 shows a structural model of a compound F321-0719, (i.e. C1CCCC1c(on2)nc2-c3cc(ccc3)NC(=O)c([nH]4)cc(c45)cccc5) docked into the 5'-adenosine monophosphate-activated protein kinase (AMPK) in accordance with an example embodiment.

Example 2: The Molecular Docking Analysis Showing that the Compound of Formula I (i.e. F321-0719) is a Direct AMPK Activator by Binding to the Kinase Pocket The binding mode of the compound F321-0719 docked into the active site of AMPK is shown in FIG. 1. The AMPK protein is represented as cartoon. AMPK and key residues around the binding pocket are shown as sticks. The hydrogen bond is labeled as red dashed line. The interactions between AMPK and F321-0719 consists of hydrophobic, polar and hydrogen bond interactions. The hydrophobic groups of F321-0719 form hydrophobic interactions with the side chain of L18, F27, K29, I46, L47 and S108. The polar groups of F321-0719 exhibits polar interactions with the side chain of I46, L31, N48, R83, S108, and N111. In addition, F321-0719 formed hydrogen bond interaction with the backbone of I46.

Example 3: The Cytotoxicity Effect of the Compound F321-0719 on NSCLC Cells H1975

Figure 2A:
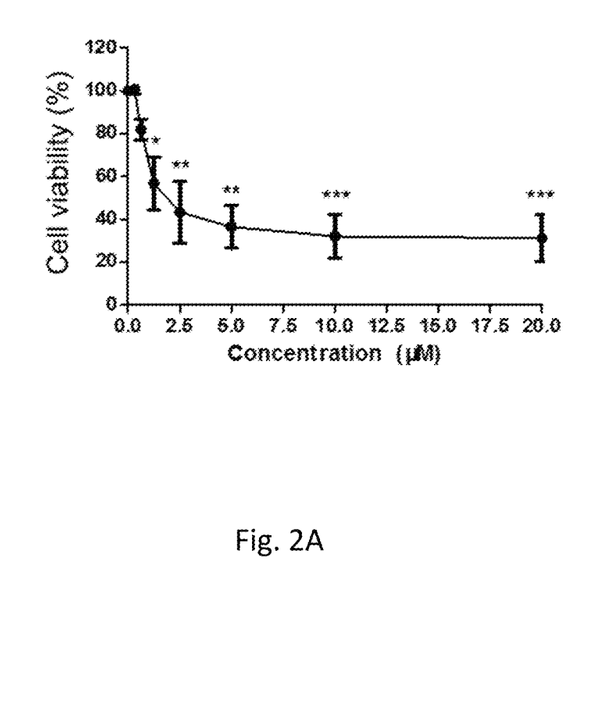
FIG. 2A shows MTT assay results showing that the compound F321-0719 decreases cell viability on H1975 NSCLC cells in accordance with an example embodiment.
Figure 2B:
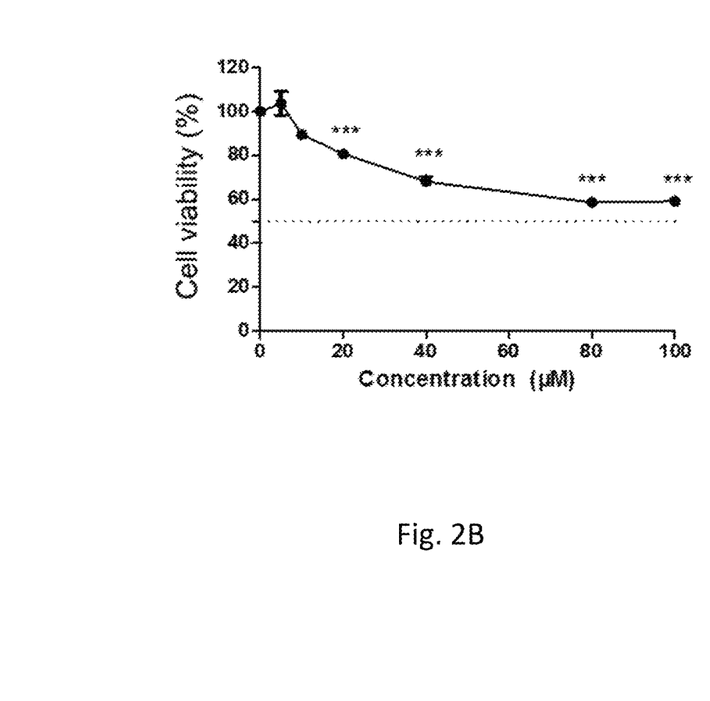
FIG. 2B shows MTT assay results showing that the compound F321-0719 exhibits no cytotoxicity on CCD-19 Lu cells in accordance with an example embodiment.

FIG. 2A shows the dosage response curve and the $IC_{50}$ of the compound F321-0719 on H1975 cells for 72 h. FIG. 2B shows the dosage response curve and the $IC_{50}$ of the compound F321-0719 on normal CCD-19 Lu cells for 72 h. All data were expressed as mean±SEM (n=3, $*p<0.05$, $p<0.01$, $*p<0.001$).

As shown in FIG. 2A, the MTT assay showed that the compound F321-0719 can inhibit cell proliferation on H1975 cells. As shown in the table 1, the $IC_{50}$ value of the compound on H1975 cells is 3.46±1.71 µM after 72 h treatment. The cytotoxicity effect of the compound on normal fibroblast CCD-19 Lu at 72 h was also analyzed. As shown in FIG. 2B and table 1, the compound exhibits no cytotoxicity on CCD-19 Lu cells even at the concentration 20 times folds than $IC_{50}$ on H1975 cells.

TABLE 1

| The cytotoxicity effect of the compound F321-0719 on H1975 and CCD-19 Lu | | |
|---|---|---|
| Cell lines | EGFR mutation | $IC_{50}$ (µM) |
| CCD-19 Lu | Normal lung cells | >100 |
| H1975 | L858R/T790M | 3.46 ± 1.71 |

Example 4: A Dose-Dependent Increase in AMPK Phosphorylation as Well as Fatty Acid Oxidation Induced by the Compound F321-0719

Figure 3A:
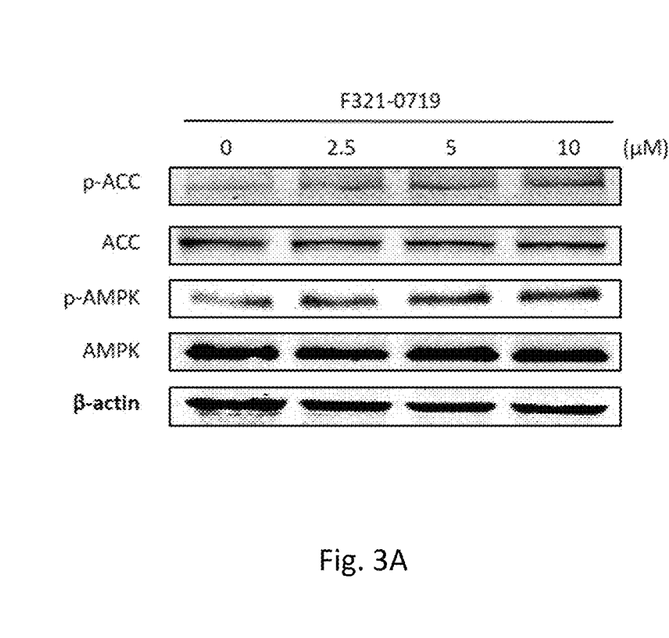
FIG. 3A shows a western blot analysis demonstrating that the compound F321-0719 induces AMPK activation in accordance with an example embodiment.
Figure 3B:
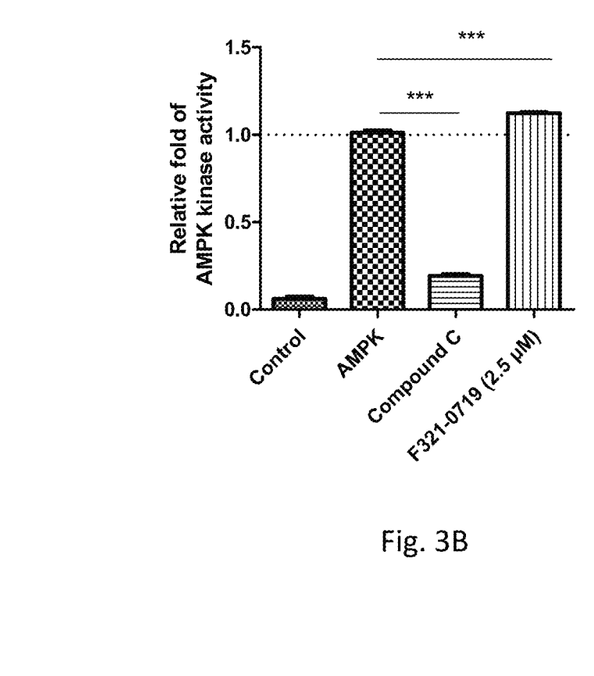
FIG. 3B shows that the compound F321-0719 enhances the AMPK activity in accordance with an example embodiment.

FIG. 3A shows that the compound F321-0719 induced the AMPK activation by phosphorylation of the AMPK and ACC on H1975 cells for 48 h. FIG. 3B shows that the compound F321-0719 has a significantly activation of AMPK enzyme (n=3, $***p<0.001$).

Previously studies demonstrated that phosphorylation of AMPK signal could activate ACC, while cancer cell proliferation requires lipids for cell membrane synthesis. As AMPK downstream, ACC is an important regulator of fatty acid oxidation. When AMPK was activated by phosphorylation on Thr 172 site, ACC was phosphorylated to increase fatty acid oxidation. Western blot analysis of FIG. 3A shows that the compound F321-0719 activated phosphorylation of both AMPK and ACC in a dose-dependent manner, indicating the anti-cancer efficacy is mediated by suppression of lipogenesis. β-actin is used as a loading control. As shown in FIG. 3B, AMPK enzyme activity assay was visually performed by the compound F321-0719. AMPK activity was enhanced at 2.5 µM of the compound F321-0719. AMPK kinase was used to indicate the basal activity level. Compound C is AMPK inhibitor used as negative control group. All enzyme activity was presented as fold of the AMPK kinase group.

Figure 4A:
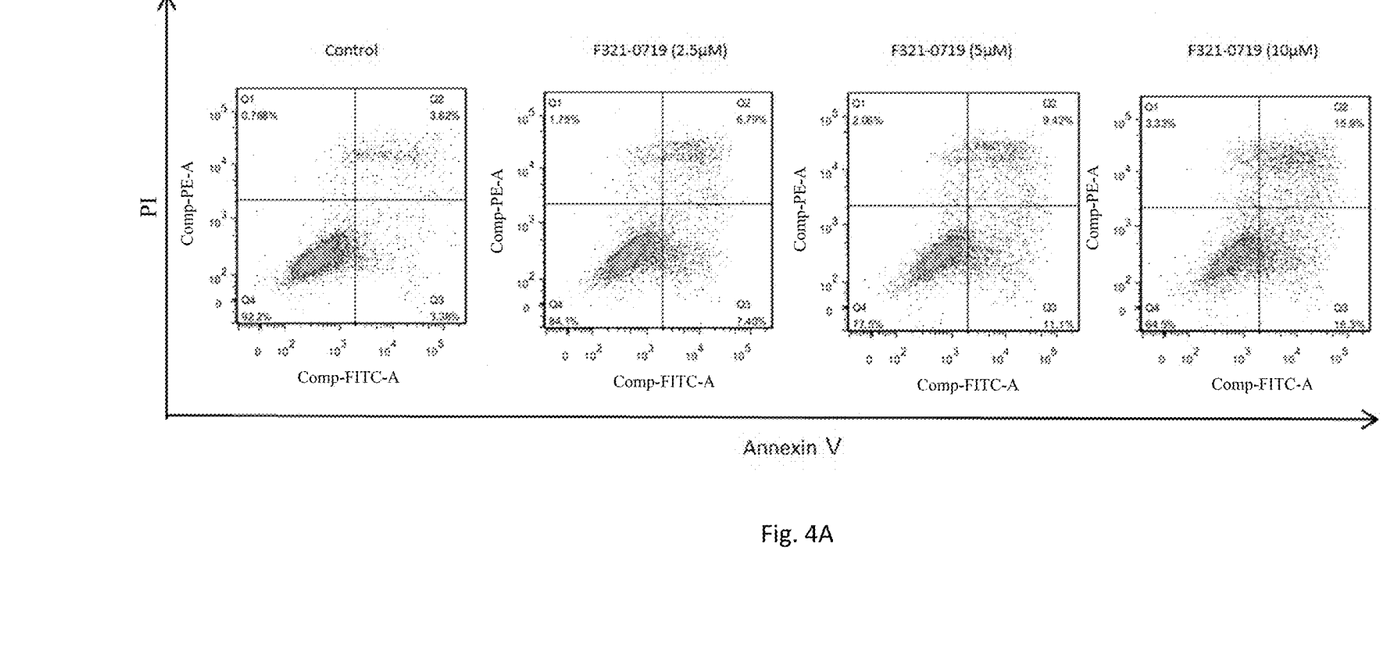
FIG. 4A shows a flow cytometric analysis on the apoptosis level of H1975 cells after the compound F321-0719 treatment for 48 h.
Figure 4B:
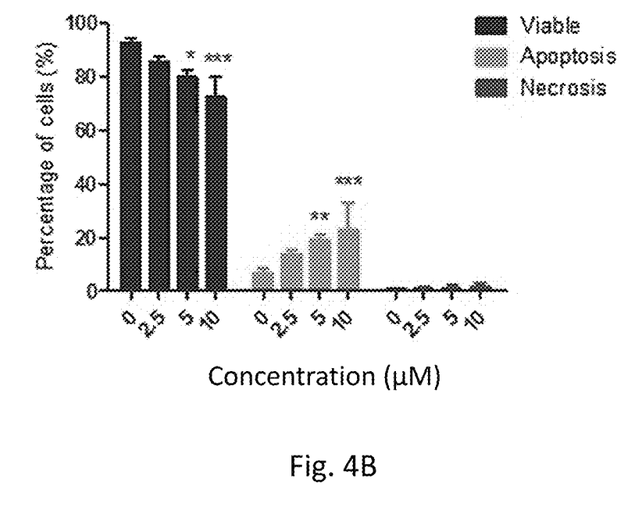
FIG. 4B shows a statistical analysis on apoptosis data of FIG. 4A.
Figure 4C:
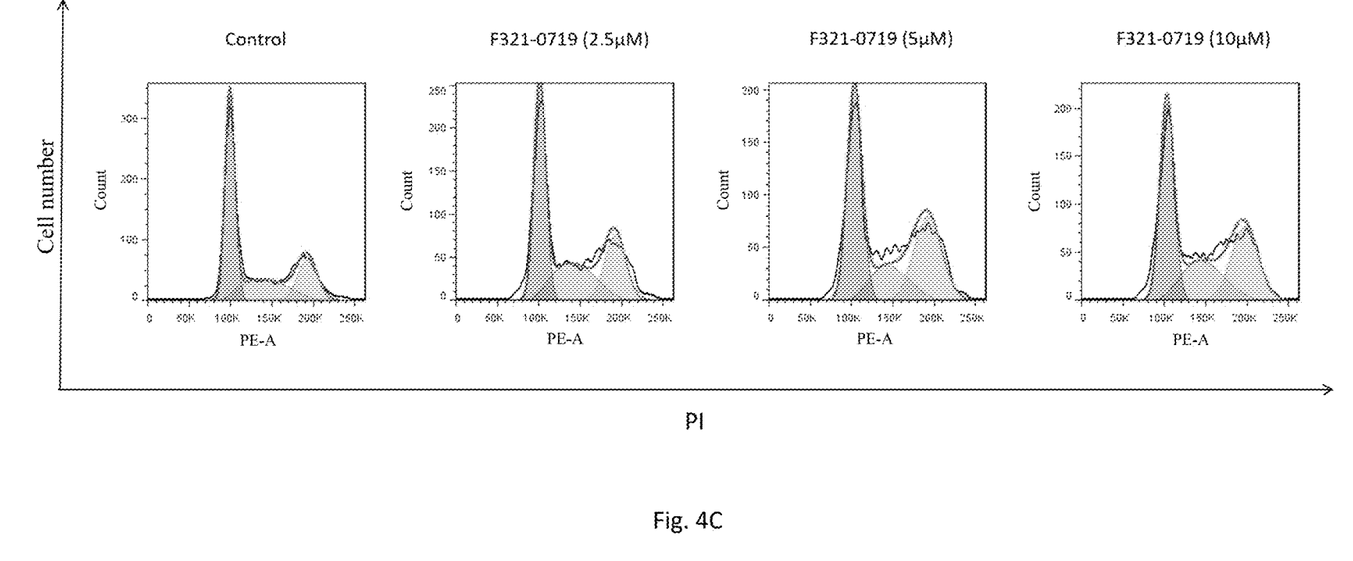
FIG. 4C shows that H1975 cells lead to G2 phase arrest with the compound F321-0719 at different concentrations for 48 h.
Figure 4D:
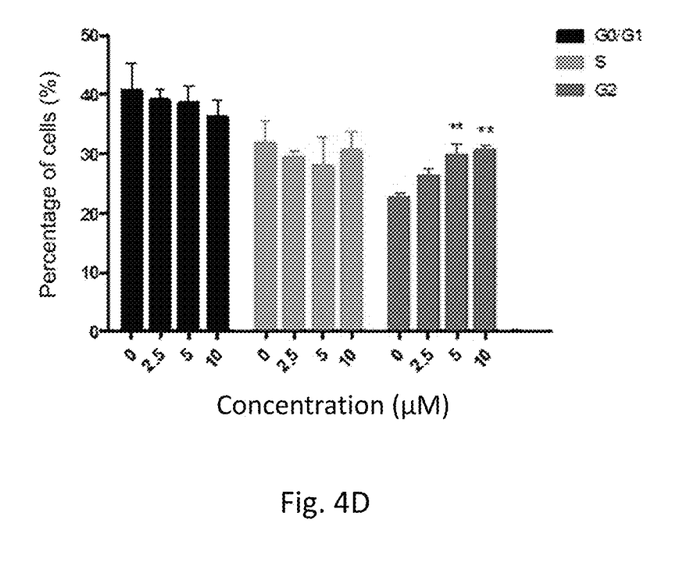
FIG. 4D shows a statistical analysis on cell cycle distribution of FIG. 4C.

Example 5: The Compound F321-0719 Significantly Induced Apoptosis and LED to Cell Cycle Arrest in H1975 Cells as Examined by Quantitative AnnexinV/PI Flow Cytometry Analysis FIG. 4A shows flow cytometric analysis of the apoptosis level after the compound F321-0719 treatment for 48 h. FIG. 4B shows the data on the percentage of viable cells, apoptosis and necrosis. FIG. 4C shows that H1975 cells led to G2 phase arrest with the compound F321-0719 at different concentration for 48 h. FIG. 4D shows cell cycle distribution for 48 h. All data was presented as mean±SEM (n=3, $*p<0.05$, $p<0.01$, $*p<0.001$).

Morphology observation by microscope, after treating H1975 cells with the compound F321-0719 for 48 h, the treated adherent cells were thin via some were floated and rounded-up at 10 µM. Then by using quantitative apoptosis measurement method, flow cytometry analysis of FIG. 4A showed that the compound F321-0719 induced significant level of apoptosis in a concentration-dependent manner. Compared with the control group, the compound F321-0719 showed significant higher level of apoptosis (FIGS. 4A-4B). Besides, after treatment by the compound F321-0719 with dose concentrations 0, 2.5, 5, 10 µM for 48 h, the cells were stained with Propidium iodide (PI). FIGS. 4C and 4D showed that at 5 μM and 10 μM, the G2 phase increased consistent with the results of flow cytometry.

Thus, the compound F321-0719 acts as the AMPK activator, targeting on the master metabolism switch-AMPK. The compound induces the apoptosis of NSCLC H1975 cells but no cytotoxicity on normal lung cells CCD-19 Lu. In one example, the compound F321-0719 can be used to treat lung cancer or NSCLC. In one example, the compound can be used to treat lung cancer/NSCLC in which the tumors have EGFR mutation. In another example, the tumors have L858R or T790M mutant EGFR. In another example, the tumors have L858R and T790M double mutant EGFR. In another example, the compound can be used to treat lung cancer/NSCLC in which the tumors develop resistance to Gefitinib.

As used herein, the term "subject" or "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

As used herein, the term "therapeutically effective amount" refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "administration" or "administering" of the subject compound refers to providing a compound of the invention and/or prodrugs thereof to a subject in need of treatment.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present invention is not to be limited in scope by the specific example embodiments described herein, since such example embodiments are intended as but single illustrations of one aspect of the invention and any functionally equivalent embodiments are within the scope of this invention.

Indeed, various modifications of the invention in addition to those shown and described herein will become apparent to those skilled in the art from the foregoing description and accompanying drawings.

What is claimed is:

1. A method of treating lung cancer in a subject in need thereof, comprising:
administering a therapeutically effective amount of a compound to the subject to treat the lung cancer, wherein the compound is presented by formula I formula I 2. The method of claim 1, wherein the lung cancer is Non-Small Cell Lung Cancer (NSCLC).

3. The method of claim 1, wherein tumors of the lung cancer include epidermal growth factor receptor (EGFR) mutations.

4. The method of claim 1, wherein tumors of the lung cancer include L858R mutant EGFR.

5. The method of claim 1, wherein tumors of the lung cancer include T790M mutant EGFR.

6. The method of claim 1, wherein tumors of the lung cancer include L858R and T790M mutant EGFR.

7. The method of claim 1, wherein tumors of the lung cancer are resistant to Gefitinib.

8. The method of claim 1, wherein the compound activates 5'-adenosine monophosphate-activated protein kinase (AMPK) to treat the lung cancer.

9. The method of claim 2, wherein tumors of the NSCLC include epidermal growth factor receptor (EGFR) mutations.

10. The method of claim 2, wherein tumors of the NSCLC include L858R mutant EGFR.

11. The method of claim 2, wherein tumors of the NSCLC include T790M mutant EGFR.

12. The method of claim 2, wherein tumors of the NSCLC include L858R and T790M mutant EGFR.

13. The method of claim 2, wherein tumors of the NSCLC develop resistance to Gefitinib.

14. The method of claim 2, wherein the compound activates 5'-adenosine monophosphate-activated protein kinase (AMPK) to treat the NSCLC.

* * * * *